(12) United States Patent
Donlon et al.

(10) Patent No.: US 12,269,968 B2
(45) Date of Patent: Apr. 8, 2025

(54) LOW VOC WATER-BORNE COLORANT COMPOSITIONS WITH IMPROVED MICROBIAL RESISTANCE AND METHOD FOR ASSESSING MICROBIAL RESISTANCE OF COLORANT COMPOSITIONS

(71) Applicant: SWIMC LLC, Cleveland, OH (US)

(72) Inventors: Jacob S. Donlon, Chesterton, IN (US); Donald Diehl, Beecher, IL (US); Patricia L. Olofsson-Elkow, Frankfort, IL (US); Renee Clayton, Crown Point, IN (US); Carl Braun, Fairview Park, OH (US); Tony A. Rook, Lakewood, OH (US)

(73) Assignee: SWIMC LLC, Cleveland, OH (US)

( * ) Notice: Subject to any disclaimer, the term of this patent is extended or adjusted under 35 U.S.C. 154(b) by 0 days.

(21) Appl. No.: 18/641,679

(22) Filed: Apr. 22, 2024

(65) Prior Publication Data

US 2024/0279492 A1    Aug. 22, 2024

Related U.S. Application Data

(63) Continuation of application No. PCT/US2022/078685, filed on Oct. 26, 2022.

(60) Provisional application No. 63/273,383, filed on Oct. 29, 2021.

(51) Int. Cl.
| | |
|---|---|
| C09D 7/41 | (2018.01) |
| C09B 67/22 | (2006.01) |
| C09D 5/02 | (2006.01) |
| C09D 7/45 | (2018.01) |
| C09D 7/63 | (2018.01) |
| C09D 7/65 | (2018.01) |
| C09D 167/06 | (2006.01) |
| C12Q 1/18 | (2006.01) |

(52) U.S. Cl.
CPC ............ *C09D 7/41* (2018.01); *C09B 67/004* (2013.01); *C09D 5/022* (2013.01); *C09D 5/028* (2013.01); *C09D 7/45* (2018.01); *C09D 7/63* (2018.01); *C09D 7/65* (2018.01); *C09D 167/06* (2013.01); *C12Q 1/18* (2013.01)

(58) Field of Classification Search
CPC ........ C09B 67/004; C09D 7/41; C09D 5/022; C09D 5/028; C09D 7/45; C09D 7/63; C09D 7/65; C09D 167/06; C12Q 1/18
See application file for complete search history.

(56) References Cited

U.S. PATENT DOCUMENTS

| | | |
|---|---|---|
| 2006/0207476 A1 | 9/2006 | Coward |
| 2011/0280961 A1 | 11/2011 | Gaglani |
| 2015/0291821 A1 | 10/2015 | Elliot |

FOREIGN PATENT DOCUMENTS

| | | |
|---|---|---|
| EP | 0980648 A1 | 2/2000 |
| JP | 2003146814 A | 5/2003 |
| JP | 2015003863 A | 1/2015 |
| WO | 2009091450 A1 | 7/2009 |

OTHER PUBLICATIONS

Mounyr Balouiri et al., "Methods for in vitro evaluating antimicrobial activity: A review" Journal of Pharmaceutical Analysis, vol. 6, No. 2, Apr. 1, 2016, pp. 71-79.

John Gillatt, et al. "The microbial resistance of polymer dispersions and the efficacy of polymer dispersion biocides—A statistically validated method," International Biodeterioration & Biodegradation, vol. 104, Mar. 25, 2015, pp. 32-37.

IBRG International Biodeterioration Research Group, "The Evaluation of Biocidal Substances and Products in Aqueous-Based Polymer Dispersions," v 6.1, Sep. 2014.

*Primary Examiner* — Anthony J Green

(57) ABSTRACT

Colorant compositions which are suitable for tinting base paint or stains in color tinting equipment and which provide improved resistance to microbial contamination by inclusion of a combination of antimicrobial agents. Also disclosed is a method for assessing the resistance of colorant compositions to microbial growth.

20 Claims, 2 Drawing Sheets

LOW VOC WATER-BORNE COLORANT COMPOSITIONS WITH IMPROVED MICROBIAL RESISTANCE AND METHOD FOR ASSESSING MICROBIAL RESISTANCE OF COLORANT COMPOSITIONS

CROSS REFERENCE TO RELATED APPLICATIONS

This application is a continuation of PCT Application No. PCT/US2022/078685 filed on Oct. 26, 2022, which claims the benefit of U.S. Provisional Application No. 63/273,383 filed on Oct. 29, 2021, each of which is incorporated herein by reference in its entirety.

FIELD OF THE INVENTION

This application generally relates to colorant compositions having improved microbial resistance resulting from the addition of a combination of antimicrobial agents. This application further relates to a method for assessing resistance of a colorant composition to microbial growth.

BACKGROUND

Architectural paint and stain manufacturers generally distribute premixed paints and stains in a small number of popular colors. To accommodate consumer desires and enable color-matching to existing painted or stained surfaces, manufacturers typically also distribute a set of tintable base paints or stains that may be tinted to a custom, selected color using equipment that adds one or more colorants to the base paint or stain, thus allowing paint to be custom-tinted to a much larger array of colors than the limited color options typically available in premixed products.

Architectural paint and stain manufacturers have tended to distribute several (e.g., 2 to 4) tintable base paints ranging from, for example, a bright white paint to a relatively unpigmented paint. Base paints and stains may employ various binders (e.g., natural or synthetic resins) and carriers (e.g., solvent or water to form a solvent-based or water-based paint or stain, respectively). Some manufacturers sell pre-colored paints (e.g., a red, a blue, and yellow colored base), which may be mixed with additional colorants at the point-of-sale. Colorants are typically distributed by colorant composition manufacturers in closed containers and are used at the color tinting equipment to refill refillable canisters for each colorant in point-of-sale color tinting equipment.

Utilizing color tinting equipment, colorants may be volumetrically metered from colorant canisters in a multiple-colorant dispensing station, with a multitude (usually 12 to 20) of colorants having different colors typically employed. After addition, the tinted paint is mixed or shaken to distribute the colorant compositions evenly throughout the base paint. Thus, by volumetrically adding one or more colorants to a base paint, a paint retailer can custom-tint a base paint to a customer's desired color. Colorants that are compatible with only water-based base coating compositions are referred to as water-only colorant compositions, whereas colorants that are compatible with both water-based and solvent-based base coating compositions are referred to as universal colorant compositions.

Like both base paints and stains and tinted paints and stains, colorant compositions are susceptible to microbial contamination in both the wet-state (e.g., liquid form), or the dry-state (e.g., dry film). Consequently, colorant compositions generally include biocides, or antimicrobials, to impart microbistatic properties to colorant compositions in both the wet-state and as a dry-film. Biocides work to kill living organisms, such as bacteria, viruses, mold, and fungus. In both base paints and stains and colorant compositions, biocides may have a wet-state preservative effect to prevent in-can or in-canister microbial spoilage, and may also have a dry-film preservative or anti-defacement effect, whereby a biocide in an prevents the growth of or inactivates bioorganisms or makes a dry film less favorable for/less susceptible to biological growth. Preservation strategies can differ between colorant compositions and paints and stains, however, because paints and stains comprise sufficient polymer to form a film upon application, whereas colorant compositions do not comprise sufficient polymer to form a film. Proper antimicrobial selection can be particularly acute for water-based colorant compositions, which generally are more susceptible microbial contamination through microbial growth than their solvent-based counterparts.

Historically, high VOC water-based colorant compositions contained low molecular weight glycols (i.e. ethylene glycol, diethylene glycol), which provided sufficient resistance to microbial contamination due to the biostatic properties of the components used in the formulations. As formulations have shifted to contain lower amounts of VOCs, the reduction of these inherently biostatic components has increased susceptibility to microbial contamination (e.g., by bacterial, fungal, yeast, or algal growth). Despite this susceptibility, lower VOC formulations may be preferred because various national and state regulations limit overall VOC and Hazardous Air Pollutants (HAPs) content, see, for example, 40 Code of Federal Regulations Part 59, National Volatile Organic Compound Emissions Standards for Architectural Coatings.

Addition of one or more wet-state preservatives to a composition may increase shelf stability of low VOC water-based colorant compositions. Wet-state preservatives include 1,2-Benzisothiazolin-3-one (BIT), and the reaction product of 5-chloro-2-methyl-4-isothiazolinone (CMIT) with 2-methyl-4-isothiazolinone (MIT). The effectiveness of certain preservatives is limited in time, however, with some sanitizers extremely short-acting, some remaining effective on a slightly longer period of days, and others remaining effective for more extended periods. In addition to effectiveness, the amount of such wet-state preservatives that can be added to a commercial product is limited by economic concerns, as well as a perception of environmental and toxicological risk. The amounts that may be added of some materials having preservative characteristics is limited by regulation in the United States through the Environmental Protection Agency under the Federal Insecticide Fungicide and Rodenticide Act (FIFRA), as well as regulation in the European Union and in other countries.

Dry-film preservation may be increased by addition of dry-state microbistat preservatives. Typical dry-film preservatives include the extender zinc oxide or a pyrithione such as sodium pyrithione or zinc pyrithione. Most dry-film preservatives, however, provide dry-film resistance to microbial growth for a limited time. Like wet-state preservatives, some materials having dry-state preservative characteristics are regulation or increased scrutiny in the United States and in other countries.

Control and prevention of microbial growth in color-tinting equipment has been particularly challenging. Although colorant preservation can be maintained through the distribution process by addition of a base amount of wet-state preservatives to the colorant, colorant compositions are exposed to microbes present in air and water when a colorant container is opened for use just prior to introduction to color tinting equipment.

Colorant preservation and prevention of microbial growth in color tinting equipment is more challenging because in use, portions of a colorant composition in a refillable colorant canister partially dry into a partial wet-state/partial dry-state. Microbial growth of partial wet-state/partial dry-state material may occur more readily due to repeated contact of the partial dry-state colorant with new liquid colorant composition as a colorant container is emptied through use and refilled. While not being limited by theory, it is believed that a cycle of evaporation and condensation of carrier occurs in a colorant container, making the partial dry-state colorant more susceptible to microbial growth.

Usage rates of colorant compositions in color tinting equipment varies, and over time (usually weeks or months), continuous environmental exposure can allow microbial growth to occur, leading to undesirable effects like visible mold growth and malodor in the refillable colorant container and contacted parts of color tinting equipment. Operators of color tint equipment are required to purge and clean refillable containers of colorant composition to clean the color tint equipment, resulting in reduced machine availability, lost time, and increased expense.

Thus, there exists a need for a low VOC, water-borne colorant composition with improved resistance to microbial growth.

Development of an acceptable microbistat package for colorant compositions has been frustrated by the lack of an adequate test method to simulate the environment for microbial growth in a color tint machine, which can occur by both wet-state and partial dry-state contamination.

For instance, ASTM D3273 calls for hanging a coated panel above inoculated soil in an environmental chamber that simulates a tropical environment. After 2-3 weeks, panels may develop mold or fungus growth that can be assessed based on defacement of the coating. D3273 assesses only dry-state resistance to microbial contamination.

ASTM D5590, titled "Standard Test Method for Determining the Resistance of Paint Films and Related Coatings to Fungal Defacement by Accelerated Four-Week Agar Plate Assay," requires adding liquid inoculum to filter paper coated with a coating. The effectiveness of this test, however, is limited when in assessing colorant compositions, which do not include a film-forming amount of binder resin. For instance, when liquid inoculum is added to paper coated with a colorant composition, the colorant disperses from the filter paper due to the absence of film-forming binder resin in colorant. In contrast, when a coating is tested under D5590, the film-forming binder resin provides resistance to such dispersion. D5590 alternatively allows liquid inoculum to be applied by spreading it on the sample and agar plate with a sterile cotton swab. Without film-forming binder resin in the colorant composition, however, such application spreads colorant composition from the filter paper to the surrounding agar, foreclosing measurement of colorant composition resistance to microbial growth. Thus, ASTM D5590 does not provide adequate testing of fungal defacement of colorant compositions.

Although useful for assessing antimicrobial resistance of colorant compositions during distribution, standard test methods for wet-state antimicrobial resistance, such as ASTM D2574-16, fail to allow evaluation of the colorant portion in a refillable container that is in a semi-dry state.

Alternatively, experimental colorant composition preservative packages may be assessed by on-site use in colorant canisters in color tinting equipment. The conditions of such simulated use can vary from trial to trial, and on-site testing does not allow for high volume testing at an acceptable speed.

Thus, there also exists a need for an improved method to test and evaluate microbial resistance of colorant compositions.

Definitions

The term "colorant composition" means a composition that can be added to (e.g., dispensed into) a point-of-sale container whose interior volume is largely (e.g., two thirds of the container volume or more) but not completely already filled with a base paint or stain, in order to alter the hue or lightness of such base paint or stain. Colorant compositions comprise pigment and a carrier but contain less than a film-forming amount of binder resin.

The term "binder resin" means a natural or synthetic polymer suitable for use in coating and finish compositions to form dried, cured, or otherwise hardened coatings or films in which the binder may represent a continuous phase.

The terms "point-of-sale" and "retail" as used herein with respect to a site, location, store or other outlet means a place at which custom-mixed paints or stains are tinted and mixed in small batch lots (e.g., one half pint, one pint, one quart, one liter, one gallon, four liter, five gallon or 20 liter containers, corresponding to containers from about 0.2 to 20 L) for sale to end-users (e.g., painters, builders and homeowners). Representative point-of-sale retail, wholesale or combined retail/wholesale outlets include paint stores, hardware stores, building supply stores (including warehouses), and distribution centers.

The term "base coating composition" as used herein means a water-borne or solvent-borne paint or stain product packaged in a largely but incompletely filled point-of-sale container with a volume of about 0.2 to 20 L equipped with an openable and recloseable lid, cap or other closure, and which may be used as is but normally will be tinted at the point-of-sale by adding one or more colorant compositions to the paint or stain product in its container, and stirring, shaking or otherwise mixing the container contents to disperse the colorant composition throughout the base paint or stain product.

The term "pigment" means a natural or synthetic particulate material having light-reflective or light-absorptive characteristics, and a surface energy and particle size suitable for use in coloring paints and other coating compositions, and includes both insoluble materials such as inorganic or organic powdered pigments, soluble materials such as organic dyes, or blends thereof.

The term "film-forming" when used in reference to a polymeric binder means that a solution or dispersion containing the polymeric binder can be coated in a thin wet layer (e.g., of about 150-200 vim thickness) on a suitable substrate and dried, cured, or otherwise hardened (with a suitable coalescent) to form over the substrate a substantially continuous dry film coating layer (e.g., of about 75-100 vim thickness) containing the polymer.

The term "comprising" and "comprises" and variations thereof do not have a limiting meaning where those terms appear in the description and claims. Thus, a composition that "comprises" a compound may also include other compounds not appearing in the description or claim.

"VOCs" are organic chemicals that have a high vapor pressure at ordinary room temperature and are defined by regulation in the United States. Part 41 Code of Federal Regulations Section 51.100(s) defines a VOC to be: "any compound of carbon, excluding carbon monoxide, carbon dioxide, carbonic acid, metallic carbides or carbonates, and ammonium carbonate, which participates in atmospheric photochemical reactions," subject to a list of exempted compounds defined in the regulation.

Examples of compounds commonly classified as VOCs include acetone, acrolein, acrylonitrile, benzene, bromodichloromethane, bromoform, bromomethane carbon tetrachloride, chlorobenzene, chloroethane, chloroform, dibromochloromethane, dichloroethane, dichloropropane, dichloropropene, diethyl ether, dioxane, ethylbenzene, methyl chloride, methyl ethyl ketone, tetrachloroethane, formaldehyde, toluene, trichloroethane, styrene, and vinyl chloride.

The term "substantially free" of a compound means that the cited material contains less than 100 ppm of the recited compound.

The term "essentially free" of a compound means that the cited material contains less than 50 ppm of the recited compound.

The term "essentially completely free" of a compound means that the cited material contains less than 10 ppm of the recited compound.

As used herein, the term "about" with reference to a number or quantity refers to the amount associated with customary error or imprecision in measurement or reporting and usual variations in raw materials.

As used herein, "a," "an", "the," "at least one" and "one or more" are used interchangeably. Thus, for example, a colorant that comprises "an" additive may include one or more additives.

As used herein, steps of a method may be performed in any order unless the context requires otherwise, such as when each method step is preceded by a letter identifying its position in sequence (e.g., a), b), c)).

Test Methods

The amount of VOC present in a composition may be measured by gas chromatography via ASTM D6886-18, titled "Standard Test Method for Determination of the Weight Percent of Individual Volatile Organic Compounds in Waterborne Air-Dry Coatings by Gas Chromatography." VOC amounts are reported in grams/Liter less exempt compounds (g/L).

Concentrations of anti-microbial additives in a colorant composition may be calculated based on amounts of active preservative added as raw materials in a composition. The active anti-microbial ingredient concentration in raw material preservatives generally are available from labels approved by the United States Environmental Protection Agency. Concentrations of active preservatives are reported in ppm by weight.

Assessment of whether a colorant composition contains a film-forming amount of polymer may be made by drying a thin film of colorant composition on a substrate, then washing the dried colorant composition with an aqueous solvent such as water. A colorant composition that contains less than film-forming amount of polymer will wash away with the solvent.

SUMMARY OF THE INVENTION

The present disclosure provides improved resistance to microbial contamination and includes, in one aspect, a colorant composition comprising an alkyl-isothiazolin-3-one in an amount of 25 ppm to 200 ppm, a halo-propynyl alkylcarbamate in an amount of 1,000 ppm to 10,000 ppm, and a secondary amino-benzimidazole in an amount of 500 ppm to 4,000 ppm, wherein the colorant composition contains less than 200 g/L VOCs, wherein the colorant contains one or more pigments and a carrier and contains less than a film-forming amount of a film-forming polymer, and wherein the colorant is suitable for addition to a base coating composition.

In some approaches, the colorant composition of the previous paragraph may contain less than 100 g/L VOCs, preferably less than 50 g/L VOCs, and even more preferably, less than 20 g/L VOCs.

In another aspect, the present invention comprises a method of making a colorant composition comprising adding to a colorant composition an alkyl-isothiazolin-3-one in an amount from about 75 ppm to about 158 ppm, adding to a colorant composition a halo-propynyl alkylcarbamate in an amount of 1000 ppm to about 9,550 ppm, and adding to a colorant composition a carbendazim in an amount of about 500 ppm to about 3,450 ppm; wherein the colorant composition is suitable for addition to a base coating composition.

In another aspect, the present disclosure includes a method of assessing microbial resistance of a colorant composition comprising:
  (a) exposing an article at least partially coated with a colorant composition to a first agar plate inoculated with spores of at least one fungal species by placing the article in the first inoculated agar plate to form a first agar plate test bed;
  (b) incubating the first agar plate test bed at an elevated temperature for a first exposure period;
  (c) removing the article from the first agar plate test bed;
  (d) exposing the article to a second agar plate inoculated with the spores of at least one fungal species by placing the article in the second inoculated agar plate to form a second agar plate test bed;
  (e) incubating the second agar plate test bed at an elevated temperature for a second exposure period; and
  (f) rating fungal coverage on the article in the second inoculated agar plate following the second exposure period according to a rating scale to generate a fungal coverage rating grade.

The foregoing approaches may be combined with one or more optional features as further described herein.

DETAILED DESCRIPTION

Figure 1:
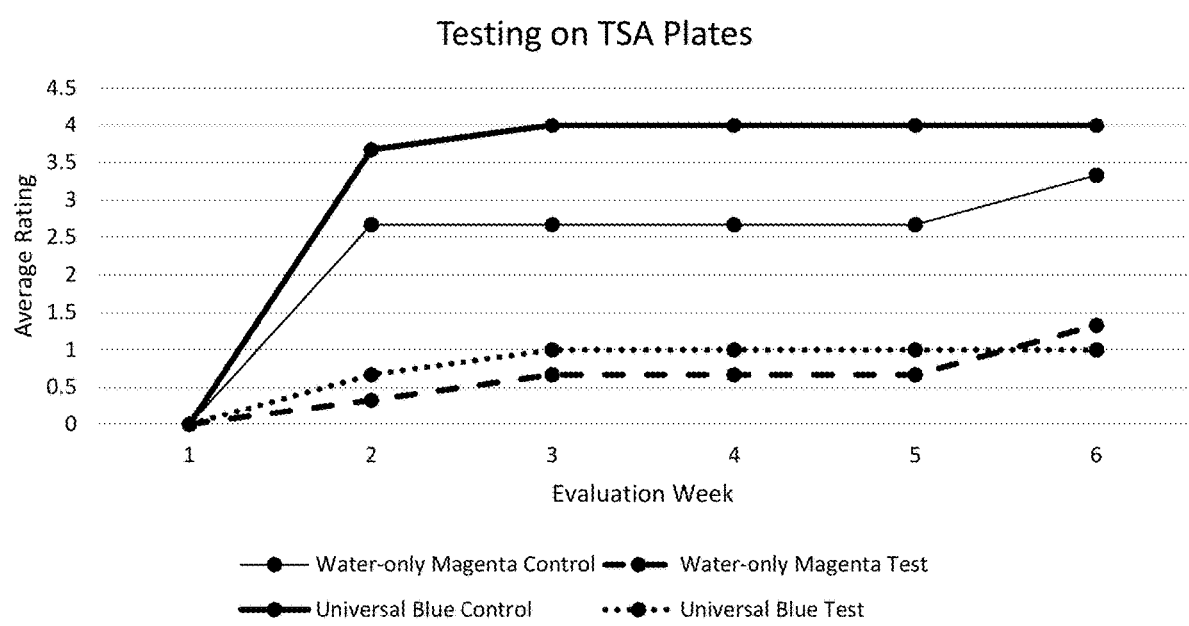
FIG. 1 is a plot of the antimicrobial efficacy of colorant compositions of the present disclosure as compared to commercially-available, water-borne colorant compositions as evaluated on TSA plates.

It has been surprisingly found in accordance with the present invention that improved colorant compositions comprising an alkyl-isothiazolin-3-one, a halo-propynyl alkylcarbamate, and a secondary amino-benzimidazole exhibit enhanced antimicrobial effectiveness as compared to compositions containing only one or two or the foregoing compounds and compounds containing only a conventional amount of wet-state preservative. Thus, a synergistic effect has been discovered of utilizing these multiple microbial additives to increase the microbial resistance of colorant compositions as compared to existing colorant compositions that include only one or two microbistatic components.

The microbial efficacy of colorant compositions of the present invention has been assessed using a novel testing method that simulates the partial wet-state/partial dry-state of colorant compositions when used in color tinting equipment. Colorant compositions of the present invention have been found to show improved anti-microbial properties according to the novel test method, which previous test methods were unable to discern.

In one aspect, the present invention comprises a colorant composition comprising an alkyl-isothiazolin-3-one in an amount of 25 ppm to 200 ppm, a halo-propynyl alkylcarbamate in an amount of 1,000 ppm to 10,000 ppm, and a secondary amino-benzimidazole in an amount of 500 ppm to 4,000 ppm, wherein the colorant composition contains less than 50 ppm VOCs, wherein the colorant composition contains one or more pigments and a carrier and contains less than a film-forming amount of a film-forming polymer; and wherein the colorant composition is suitable for addition to a base coating composition.

Colorant compositions of the present invention include an alkyl-isothiazalin-3-one, preferably 2-methyl-4-isothiazalin-3-one. Alkyl-isothiazolin-3-ones of the present invention have the following structure:

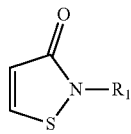

where $R_1$ is a linear or branched chain alkyl group having 1-8 carbons.

In a preferred embodiment, the alkyl-isothiazolin-3-one is preferably 2-methyl-4-isothiazalin-3-one (MIT), which has the following structure:

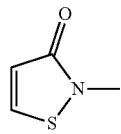

MIT is available commercially as a component of Proxel MB™, Proxel™ DMB, Proxel™ CMC-E, and Proxel™ BC Preservative from Lonza Specialty Ingredients; ActicideR RS, Acticide® GA, Acticide® LA, Acticide® MBS, Acticide® CBM 2, Acticide® MBL, ActicideR MBZ 4, Acticide® M20S, Acticide® MBS 2550 from Thor Corporation; Nipacide® FC, Nipacide® BNK, Nipacide® CI, Nipacide® CI 15HS, Nipacide® CI 15 MV, Nipacide® HF1, and Nipacide® CFX 3 from Clariant Corp.; Preventol® BP-15, Preventol® BP-509, Preventol® BM5, Preventol® BM25, Preventol® BM75, and Preventol® BMP from Lanxess Corp.; Kathon® LX, Kathon® CG/ICP II and Bioban 557 from Dow Corporation; and Mergal® MC14, Mergal® K9N, Mergal® K14, Mergal® K12N, and Mergal® 760 from Troy Corporation.

Colorant compositions of the present invention also contain a halo-propynyl alkyl carbamate, preferably 3-iodo-2-propynyl butyl carbamate. Halo-propynyl alkyl carbamates of the present invention have the following structure:

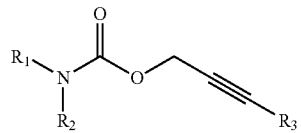

where R1 and R2 are H or linear or branched chain alkyl groups having 1-7 carbons, and where R3 is a halogen atom (F, Cl, Br, I, or At).

Preferably the halo-propynyl alkyl carbamate is 3-iodo-2-propynyl butylcarbamate (IPBC), which has the following structure:

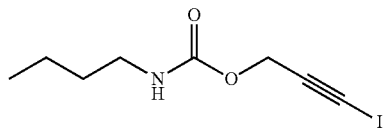

IPBC is available commercially as a component of Omacide™ IPBC 100, Omacide™ IPBC 20, Omacide™ IPBC 30, and Omacide™ IPBC 40 from Lonza Specialty Ingredients; Bioban® IPBC 20 and Bioban® IPBC 40LE from Dow Corporation; Preventol® A 31-D, and Preventol® A40, Preventol® MP100, Preventol® MP 200, Preventol® MP 260, Preventol® MP 330, Preventol® MP 360, Preventol® MP 400-D, Preventol® MP 700 from Lanxess Corporation; Acticide® MKW 2, Acticide® IPD 30, Acticide® IPS 40, Acticide® IPW40, and Acticide® IPW50 Acticide® IMS from Thor Specialties, Inc.; Polyphase® 663, Polyphase® 678, Polyphase® 662, Polyphase® PW40, Polyphase® P100, Polyphase® AF1, Polyphase® P20T, Polyphase® 600, Polyphase® 641, and Polyphase® 2085, available from Troy Corporation.

Colorant compositions of the present invention also comprise a secondary amino-benzimidazole, preferably carbendazim. Secondary amino-benzimidazoles of the present invention have the following structure:

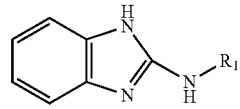

where $R_1$ is a carboxylate or ester group comprising at least 2 oxygen atoms.

Preferably, the secondary amino-benzimidazole is carbendazim (N-benzimidazolyl-2-carbamic acid methyl ester), which has the following structure.

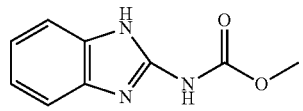

Carbendazim may be provided alone or as a mixture with other microbistat or non-microbistat ingredients. Carbendazim is available commercially as a component of Polyphase® 678, available from Troy Corporation; and in Biox® M 148, Biox® M 248, Biox® AM139, Biox® AM146, Preventol® A14D, Preventol® BCM, from Lanxess Corporation.

Colorant compositions of the present invention are water-based and include at least water as a carrier.

Colorant compositions of the present invention comprise one or more pigments. When a colorant composition is added to a base paint, pigments add color to the base paint and may impact the gloss or flatness of the paint. A pigment may be an inorganic or organic powdered pigment or a soluble material such as an organic dye or blends thereof. Examples of organic pigments include anthraquinone pigments; quinophthalone pigments; isoindoline pigments; nitroso pigments; perinone pigments; quinacridone pigments; perylene pigments; pyrropyrrol pigments; and dioxazine pigments. Example of inorganic pigment include carbon pigments such as carbon black; chromate pigments; sulfide pigments; oxide pigments; hydroxide pigments; ferrocyanide pigments; silicate pigments; phosphate pigments; and others (such as cadmium sulfide and cadmium selenide). Pigments are available in a wide variety of colors, including whites, such as titanium dioxide, zinc oxide, and zinc sulfide; reds, such as cadmium sulfide, selenite, and iron oxide; yellows, such as cadmium sulfide, lead chromate, and iron oxide; greens, such as chromium oxide green; blues, such as iron, ultramarine, and cobalt blues; and blacks, such as carbon black. Pigments may also include metallic flakes and natural and synthetic inert extender pigments, for example, kaolinite, mica, calcium carbonate, silica, barium sulfate, and talc.

A pigment may also be a light fast dye, which may provide resistance to fading upon exposure to natural light. Amongst light fast dyes, light fast metal complex dyes are particularly useful. Metal complex dyes may include 1:1 or 1:2 metal complexes of azo or azomethine dyes or metallized phthalocyanines, such as copper phthalocyanine or nickel phthalocyanine: as well as other 1:1 nickel complexes, 1:1 cobalt complexes, 1:1 copper complexes, 1:1 chromium complexes, 1:1 iron complexes or symmetrical or asymmetrical 1:2 cobalt complexes, 1:2 iron complexes or 1:2 chromium complexes. Suitable metal complex dyes may include those that are available commercially under the designation Neozapon®. from BASF, Orasol® from Ciba-Geigy, or Savinyl® from Clariant Pigments & Additives.

A pigment may also include functional fillers, which are non-water soluble solids. Functional fillers may include solids which provide additional functional characteristics to the paint, for example, intumescent ingredients, such as ammonium polyphosphates, melamines, pentaerythritol and similar compounds.

Colorant compositions of the present invention may include a wide variety of pigments or combinations of pigments, selected to generate an array of colorants of various colors of the color spectrum, which may be added alone or in combination via color tinting equipment to tint a base paint or coating.

Unlike a base paint or stain to which a colorant composition is added, colorant compositions of the present invention contain less film-forming polymer than is required to form a film, and preferably substantially no or essentially no film-forming polymer. Film-forming polymers include a latex resin, usually selected from acrylics, vinyl acrylics, or styrene acrylics. Thus, when a colorant composition is dried and washed with water, a colorant composition will wash away due to the lack of sufficient film-forming polymer to form a film, whereas a base paint or stain will remain due to the structural stability provided from the film-forming polymer.

In some embodiments, colorants of the present invention are substantially free, essentially free, or essentially completely free of added microbistats that are not an alkyl-isothiazolin-3-one, halo-propynyl alkyl carbamate, or a secondary amino-benzimidazole. Such microbistats may include a dicyanobutane, or a pyrithione.

In some embodiments, colorants of the present invention are substantially free, essentially free, or essentially completely free of an isothiazolin-3-one that is not a methyl-isothiazolin-3-one. Such compounds have the following structure:

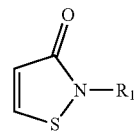

where R1 is a linear or branched chain alkyl group having 2-8 carbons.

In some embodiments, the colorant is substantially free, essentially free, or essentially completely free of a dicyanobutane, such as 1,2-dibromo-2,4-dicyanobutane.

In some embodiments, the colorant does not require additional dry-state preservatives and thus is substantially free, essentially free, or essentially completely free of zinc oxide.

Colorants of the present invention are generally compatible with and may be used for both alkyd and latex paints.

Additional components that are optionally present in the colorant composition include additional pigments, a carrier, a base, humectants (e.g., a polyether), surfactants, additional biocides, defoamers, extenders, thickeners, pH modifiers, and carboxyl-containing polymers, such as polyacrylates, and/or carboxyl-containing polyurethanes, which can function as conventional dispersing agents.

Carriers for the present invention are water-based but may include additional optional solvents that are added separately or as part of a mixture with water. Additional solvents must be selected so as not to undesirably increase VOC content. If used as a carrier, water may be tap, deionized, distilled, reverse osmosis or recycled water. Exemplary solvents that may be present in a carrier include alcohols (e.g., ethanol); esters (e.g., butyl acetate, methoxypropyl acetate and propylene glycol monomethyl ether acetate); ketones (e.g., acetone, methyl ethyl ketone, methyl isoamyl ketone and methyl isobutyl ketone; ester/ketone mixtures (e.g., ethyl 3-ethoxypropionate/methyl ethyl ketone mixtures); aliphatic solvents (e.g., white spirit, mineral spirit, petroleum distillates, paraffin solvent or vegetable oils); mixtures of aromatic solvents and ethers; and universal solvents that will work with both latex and oil-based paints (e.g., ethylene glycol, propylene glycol, hexylene glycol and glycol/water mixtures).

The humectant component, however, is an especially preferred optional component for dilution and polar control of dispersants that may be present in the colorant composition. Humectants may include polyethers such as polyalkyl glycols, such as low to moderate molecular weight polyethylene and polypropylene glycols; polyhydroxy ethers, such as those formed from epoxide polymerization; ethylene glycol polyethers; ethylene and propylene glycols; hexylene glycols; polysaccharide compounds, such as polysorbitan and polysorbitol; glycerin, sorbitol, sodium polyglutamate; modified urea compounds; and polyalkylene oxides, such as polyethylene and polypropylene oxide. Particularly useful commercial polyethylene glycols are PEG 300, PEG 400, or PEG 600. Rather than using a polyether, a dihydric or polyhydric alcohol may be employed as a humectant. Ethylene glycol is an exemplary dihydric alcohol. Ethylene glycol, however, is a VOC and as such is not preferred in practicing the invention. Propylene glycol is an exemplary polyhydric alcohol.

The coating composition may also comprise one or more surfactants such as those disclosed in U.S. Pat. No. 8,242,206. Exemplary surfactants include bis(tridecyl)ester of sodium sulfosuccinic acid (anionic) (Aerosol TR-70S), Lecithin, Lecithin without residual oil (Dry Lecithin), Lecithin with a nonionic surfactant (W/D Lecithin), fatty acid modified polyesters (EFKA 6220), nonyl phenol ethoxylates (Igepal CO 430 and Igepal CO 530), linear alcohol ethoxylates (L-12-3 and L-24-4), alkyl polyethylene glycol ethers formed from a C10-alcohol and ethylene oxide (Lutensol XP40 and Lutensol XP50), ethylene oxide/propylene oxide block copolymer (Pluronic L64), Secondary alcohol ethoxylates (Tergitol 15-S-3 and Tergitol 15-S-5), tetrafunctional ethylene oxide/propylene oxide block copolymer, nonionic (Tetronic 901 and Tetronic 90R4), Alkyl aryl polyether alcohol with nonionic solubilizer (Triton X-207), NPE Phosphate ester, anionic (Dextrol OC-50), alkyl ammonium salts of low molecular weight polycarboxylic acid polymers (Disperbyk), dinonyl sulfosuccinate (Nekal 25L), difunctional propylene oxide/ethylene oxide block copolymer (with secondary —OH groups) (Pluronic 25R4), APE dodoxynol-6 (RC-520), and the like. Many of these surfactants are available in a commercial form. The commercial names are listed in parenthesis, herein above.

Presently preferred alkyd-compatible surfactants include for example, bis(tridecyl)ester of sodium sulfosuccinic acid (anionic) (Aerosol TR-70S), Lecithin, Lecithin w/o residual oil (Dry Lecithin), Lecithin with a nonionic surfactant (W/D Lecithin), secondary alcohol ethoxylates (Tergitol 15-S-3 and Tergitol 15-S-5), Linear alcohol ethoxylates (L-12-3), alkyl aryl polyether alcohol with nonionic solubilizer (Triton X-207), alkyl polyethylene glycol ethers formed from a C10-alcohol and ethylene oxide (Lutensol XP50), and the like.

Examples of suitable latex-compatible surfactants include surfactants such as, for example, NPE Phosphate ester, anionic (Dextrol OC-50), alkyl ammonium salts of low molecular weight polycarboxylic acid polymers (Disperbyk), nonyl phenol ethoxylates (Igepal CO 530 and Igepal CO-630), alkyl polyethylene glycol ethers formed from a C10-alcohol and ethylene oxide (Lutensol XP50 and Lutensol XP60), dinonyl sulfosuccinate (Nekal 25L), difunctional propylene oxide/ethylene oxide block copolymer (with secondary —OH groups) (Pluronic 25R4), APE dodoxynol-6 (RC-520), Secondary alcohol ethoxylates (Tergitol 15-S-5), nonionic polyethylene thioethers, (Alcodet 218), modified polyalkoxylates with groups having acidic affinity (BYK 2091), dodecyl phenol ethoxylates (DD-10), high molecular weight block copolymers with groups having basic affinity (Disperbyk 184), preneutralized acrylic polymers, (EFKA 4580), alkylaryl polyglycol ethers (Emulsifier W), anionic polyelectrolyte sodium salts of polycarboxylic acids (Hydropalat 44), blend of NPE and sodium salt of Dibutylnaphthalene Sulfonate (Igepal CTA-639W), hydrophobic copolymer of polycarboxylic acid (Nopcosperse 100), propylene oxide/ethylene oxide difunctional block copolymer (with secondary —OH groups) (Pluronic 17R4 or Pluronic 25R4), ethylene oxide/propylene oxide block copolymer (Pluronic L44, Pluronic L64, and Pluronic F68), PEG 40 hydrogenated Caster oil (Surfactol 365), surfactant blends (Surfynol CT-121), salts of hydrophilic or hydrophobic copolymers of polycarboxylic acid (Tamol 1124, Tamol 731, Tamol 681 or Tamol 165), low foaming nonionic surfactant such as Triton CF-10, and the like. Many of these surfactants are available in a commercial form. The commercial names are listed in parenthesis, herein above.

Presently preferred latex-compatible surfactants include for example, alkyl polyethylene glycol ethers formed from a C10-alcohol and ethylene oxide (Lutensol XP50 and Lutensol XP60), secondary alcohol ethoxylates (Tergitol 15-S-5 and Tergitol 15-S-9), propylene oxide/ethylene oxide difunctional block copolymer (with secondary —OH groups) (Pluronic 17R4), ethylene oxide/propylene oxide block copolymer (Pluronic L44), alkylaryl polyglycol ethers (Emulsifier W), amine salts of hydrophylic copolymers of polycarboxylic acid (Tamol 731), and the like.

Non-limiting examples of universal surfactant packages are Lecithin, Tamol 731, and Tergitol 15-S-5; Dry Lecithin, Aerosol TR70S, SMA1440H, Pluronic 17R4, and Lutensol XP50; Dry Lecithin, Aerosol TR70S, SMA1440H, and Pluronic 17R4; Lecithin, Pluronic 17R4, and Lutensol XP50; Tamol 731, Dry Lecithin, and Pluronic L35; Dry Lecithin, Lecithin, Lutensol XP50, Tergitol 15-S-5, and Pluronic 17R4; and Tamol 731, Dry Lecithin, and Pluronic L44.

A defoaming agent may be added for ease of manufacture. Defoamers useful in practicing the present invention include materials such as, for example, mineral oil, silica oil (Drew L-474), and organically modified silicone oils (Drew L-405).

Additional biocides may be added to the colorant composition as a base-wet-state preservative to resist microbial growth during manufacturing, distribution, or storage. The additional biocides may include chlorinated hydrocarbons, BIT, organometallics, halogen-releasing compounds, metallic salts, organic sulfur compounds, quaternary ammonium compounds and phenolics.

The composition also may comprise one or more quick-kill sanitizers to assist in microbial growth resistance during manufacturing. Such sanitizers may include 2,2-dibromo-3-nitrilopropionamide (DBNPA), formaldehyde, glutaraldehyde, hydrogen peroxide, sodium hypochlorite, calcium hypochlorite, thiomersal, or chlorhexidine.

Extender particles may also optionally be present in the disclosed colorant compositions. Exemplary extender particles include calcium carbonate, calcium sulfate, barium sulfate, mica, clay, calcined clay, feldspar, nepheline, syenite, wollastonite, diatomaceous earth, alumina silicates, non-film forming polymer particles, aluminum oxide, silica, talc, mixtures thereof and other materials that will be familiar to persons having ordinary skill in the art. The chosen extender pigment types and amounts may vary widely and normally will be empirically determined using techniques that will be familiar to persons having ordinary skill in the art.

The colorant composition also may include one or more thickeners to increase the overall viscosity of the colorant composition. Exemplary thickeners include cellulose ethers; carboxymethyl cellulose; alginates; caseinates; hydrophobically-modified cellulose ethers; polyethylene oxide; polyvinyl alcohol; polyacrylamide; alkali soluble acrylics and styrene/maleic anhydrides; alkali swellable crosslinked acrylic emulsions, such as hydrophobically-modified alkali-swellable emulsions; and nonionic associative thickeners, such as hydrophobically modified polyurethanes and polyethers. Thickeners for alkyd-compatible surfactants include bentonite clays, organoclays, synthetic silicas, castor oil derivatives, modified acrylic copolymers, polyethylene glycol, polymerized oil derivatives, organic esters, and complex polyolefins.

The colorant composition may also comprise one or more pH modifiers. Preferred pH modifiers can be amine-based such as ammonia, ammonium hydroxide, Vantex® T (available from Eastman Chemical Company), AEPD® VOX 1000 (available from Angus Chemical Company), AMP95™ (available from Angus Chemical Company), or glucamine; or inorganic-based, such as potassium hydroxide, sodium hydroxide, or calcium hydroxide.

In another aspect, the present invention comprises a novel method of assessing microbial resistance of a colorant composition (hereinafter the "Colorant Microbial Resistance Test").

Preparation of Colorant Composition Sample

To test a colorant composition, a colorant composition sample is prepared by depositing it on a flat, clean, porous article, preferably ashless paper. Whatman Grade 41 one-inch diameter ashless filter paper is preferably utilized. In some embodiments, fiberglass filter paper may be utilized. Any suitable shape article may be utilized, and if a circular article is utilized, any suitable diameter may be utilized. Any suitable method may be employed to deposit a thin layer the colorant composition on the paper, including painting via brush, drawdown, roller, or dropper.

Preparation of Fungal Inoculated Agar Plates

Fungal inoculants are prepared and isolated for testing by allowing them to grow on potato dextrose agar (PDA) at approximately 25° C. in a high humidity environment (>85% relative humidity) until sporulated, which typically occurs in 7-10 days. Any suitable nutrient agar encouraging of growth of fungus, such as dichloran rose bengal agar (DRBC), potato dextrose agar (PDA), sabouraud dextrose agar (SDA), tryptic soy agar (TSA), or malt extract agar (MEA) may be utilized. One or more anti-microbial agents may be added to the agar to prevent bacterial growth. Following sporulation, fungal spores are harvested using 12 mL of sterile 0.1% Polysorbate 80 in deionized water. Any surfactant suitable to disperse fungal spores without biocidal impact may be used as diluent for harvesting. Preferably environmentally isolated *Aspergillus niger* or *Penicillium citrinum* are prepared as spore suspensions.

Equal amounts of each harvested spore suspension are mixed together and the population is adjusted to a suitable concentration, typically between $1\times10^5$ CFU/mL and $1\times10^8$ CFU/mL and preferably $1\times10^6$ CFU/mL, by dilution of sterile nutrient salts solution as in ASTM D-5990. Population concentration is determined via a standardized spectrophometric method or a hemocytometric method using a hemocyctometer, which is available from multiple major laboratory suppliers such as Thermo-Fischer and Sigma-Aldrich. 200 uL of the mixed fungul inoculum is transferred to an Sabouraud Dextrose Agar (SDA) plate or a plate containing another suitable nutrient agar such as DRBC, PDA, TSA, or MEA. The inoculum is spread evenly over the entire surface of the agar plate using an L-shaped cell spreader.

Deposition of Colorant Sample in Fungal Inoculated Agar Plates

After the inoculum absorbs into the agar, a colorant composition sample is placed in the center of the inoculated agar plates. The SDA plates are incubated at 25° C.-30° C. in an environmental test chamber. After one week, agar plates are assessed for defacement.

Preferably, assessment of colonization after 1 week is performed according to the rating scale described herein. Colonization in a first inoculated SDA plate after 1 week of incubation is indicative of inadequate microbial resistance. Prepared colorant composition samples not showing colonization after 1 week of incubation are transferred to a second fungal inoculated agar plate. After transfer to a second fungul inoculated agar plate, the second fungul inoculated agar plate is then incubated at 25° C.-30° C. in an environmental test chamber until at most failure of the sample, which occurs upon full defacement. Preferably, the inoculated agar plate is incubated up to six weeks.

Defacement from fungal growth on colorant composition samples in the second fungal inoculated SDA are graded weekly, preferably up to six weeks, or until rating is impossible due to overgrowth of microbes.

Rating of microbial resistance of colorant composition samples is performed according to a rating scale, preferably a numerical or alphabetical scale consisting of more than one sequential indicator each corresponding to an amount of fungal coverage on the colorant composition sample of the second fungal inoculated SDA plate.

More preferably, the rating scale is as follows:

| Rating | Growth Amount |
| --- | --- |
| 0 | No Growth |
| 1 | Trace Growth (<10% Coverage) |
| 2 | Light Growth (10-30% Coverage) |
| 3 | Medium Growth (30-60% Coverage) |
| 4 | Heavy Growth (60-100% Coverage) |

Where a rating of 3 of higher is indicative of inadequate colorant composition resistance to microbial growth. A rating of less than 3 signifies the colorant adequately resists microbial growth.

While not being bound by theory, it is believed that this novel test simulates exposure of a partial dry-state colorant composition in a colorant container. Specifically, it is believed that this test method simulates repeated washings of partial dry-state colorants as occurs in color tinting equipment, and thus simulates leaching of preservative from the partial dry-state material.

Example I: Testing Via Conventional Wet-State Antimicrobial Evaluation Methods

Colorant samples including varying preservative packages were tested using a modified form of ASTM test method D2574-16, titled "Standard Test Method for Resistance of Emulsion Paints in the Container to Attack by Microorganisms."

Duplicate 50 mL liquid colorant composition samples were challenged by inoculation with 1 mL of prepared fungal spore suspension of an *Aureobasidium* species, a *Penicillium* species, an *Aspergillus* species, a *Cladosprium* species, and an *Alternia* species, having a total culture population of $1.20\ 10^5$ CFU/mL on Day 0, $1.10\ 10^5$ CFU/mL Day 7, and $1.20\ 10^4$ CFU/mL on Day 14. Incubation at 30° C.±2° C. followed each challenge, after which each sample was evaluated for microbial contamination 72 hours and 7 days after each challenge. Microbial contamination evaluations were conducted by spreading the sample evenly on an agar plate using aseptic techniques and incubating the agar plate at 30° ° C. for 72 hours. Agar plates were then evaluated via the following rating scale:

TABLE 1

Rating Scale for Conventional Wet-State Antimicrobial Evaluation

| # Colonies on Agar Plate | Descriptive Rating | Rating |
| --- | --- | --- |
| No growth | Clean | 1 |
| 1-5 | Slight | 2 |
| 6-10 | Moderate | 3 |
| 11-25 | Moderate | 4 |
| 26-50 | Moderate | 5 |
| 51-100 | Moderate/Severe | 6 |
| 101-200 | Severe | 7 |
| 201-300 | Severe | 8 |
| Too numerous to count with rough colony edges | Severe | 9 |
| Too numerous to count with smooth colony edges | Severe | 10 |

Three representative samples of colorant compositions having the following components were prepared.

TABLE 2

Components Present in Compositions 1-3 in Weight Percent Based on Total Components in Colorant Composition

| Component | Composition 1 | Composition 2 | Composition 3 |
| --- | --- | --- | --- |
| Water | 36.23 | 22.50 | 25.52 |
| Extenders/Dispersents | 14.65 | 42.44 | 34.25 |
| Humectant | 11.62 | 5.70 | 10.49 |
| pH Buffer | 0.23 | 0.76 | 0.07 |
| Quick-kill Dispersant | 0.25 | 0.25 | 0.25 |
| | | | 6.66 |
| Surfactant | 7.68 | 6.23 | 1.05 |
| Thickener | 2.28 | | |
| Defoamer | 0.88 | | |
| Inert Pigment | 17.18 | 14.24 | 13.16 |
| Blue pigment | 9.00 | 7.88 | 8.56 |
| Total Weight Percent | 100.00 | 100.00 | 100.00 |

Additional preservatives shown in Table 3 below were added to the colorant compositions of Table 2, and the modified colorants were ground using zirconium mill beads to a 7 Hegman fineness of grind value.

TABLE 3

Active Biocide Concentration (ppm) in Colorant Compositions 1-3 Based on Total Components of Colorant After Preservative Addition.

| Biocide Package | ppm | | | | |
| --- | --- | --- | --- | --- | --- |
| | CMIT | MIT | BIT | IPBC | Zinc Pyrithione |
| A | 32 | 104 | 586 | 874 | 1520 |
| B | 19 | 6 | 400 | 0 | 1520 |
| C | 14 | 55 | 420 | 0 | 1140 |
| D | 16 | 110 | 210 | 498 | 0 |
| E | 18 | 6 | 0 | 874 | 1520 |

Evaluation data indicated no growth was shown, as indicated by the ratings of "1" throughout the evaluation period.

TABLE 4

Evaluation Rating of Colorant Composition Samples with Preservative Addition Tested According to ASTM D2574-16.

| Colorant Composition | Biocide Package | Challenge 1 | | Challenge 2 | | Challenge 3 | |
| --- | --- | --- | --- | --- | --- | --- | --- |
| | | 72 Hours | 7 Days | 72 Hours | 7 Days | 72 Hours | 7 Days |
| 1 | A | 1 | 1 | 1 | 1 | 1 | 1 |
| 1 | B | 1 | 1 | 1 | 1 | 1 | 1 |
| 1 | C | 1 | 1 | 1 | 1 | 1 | 1 |
| 1 | D | 1 | 1 | 1 | 1 | 1 | 1 |
| 1 | E | 1 | 1 | 1 | 1 | 1 | 1 |
| 2 | A | 1 | 1 | 1 | 1 | 1 | 1 |
| 2 | B | 1 | 1 | 1 | 1 | 1 | 1 |
| 2 | C | 1 | 1 | 1 | 1 | 1 | 1 |
| 2 | D | 1 | 1 | 1 | 1 | 1 | 1 |
| 2 | E | 1 | 1 | 1 | 1 | 1 | 1 |
| 3 | A | 1 | 1 | 1 | 1 | 1 | 1 |
| 3 | B | 1 | 1 | 1 | 1 | 1 | 1 |
| 3 | C | 1 | 1 | 1 | 1 | 1 | 1 |
| 3 | D | 1 | 1 | 1 | 1 | 1 | 1 |
| 3 | E | 1 | 1 | 1 | 1 | 1 | 1 |

It would have been expected that samples including lower amounts of biocides, such as Biocide Package C, would have shown decreased resistance to microbial growth relative to samples that included greater amounts of biocides. The test, however, indicated no difference between each biocide package, regardless of differences in biocide types and amounts. Thus, ASTM D2574-16 was inadequate to distinguish between the antimicrobial capabilities of the biocide packages.

Example II: Testing Via Novel Microbial Test Method

Colorant samples were prepared containing conventional extenders/dispersants, humectants, pH buffers, quick-kill and base wet-state preservatives, surfactants, thickeners, and defoamers in the amounts below and adjusted to reach tint strength specification by addition of water or extender dispersion.

TABLE 5

Composition of Colorant Samples

| Component | Parts |
| --- | --- |
| Water | 35.82 |
| Extender/Dispersent | 13.72 |
| Humectant | 11.60 |
| pH Buffer | 0.23 |
| Quick-kill and base wet-state preservative | 0.4 |
| Surfactant | 7.67 |
| Thickener | 2.31 |
| Defoamer | 0.88 |
| Inert Pigment | 17.15 |
| Blue Pigment | 8.98 |

To the prepared colorant samples, additional preservatives shown in the Table below were added and the modified colorant compositions were ground using zirconium mill beads to a 7 Hegman fineness of grind value. Microbial resistance of the resulting compositions were tested in duplicate via the novel method described herein. Average rating values after each week of growth are shown.

TABLE 6

Average Microbial Growth Ratings of Preservative Packages in Colorant as Compared to Control

| Sample | Zinc Pyrithione | IPBC | MIT | Carbendazim | BIT | Evaluation Week | | | | | | |
|---|---|---|---|---|---|---|---|---|---|---|---|---|
| | | | | | | 1 | 2 | 3 | 4 | 5 | 6 | 7 |
| Control | 1520 | 880 | 5 | 0 | 0 | 0 | 1 | 4 | 4 | 4 | 4 | 4 |
| 1 | | 880 | 5 | 0 | 0 | 0 | 4 | 4 | 4 | 4 | 4 | 4 |
| 2 | 1520 | 880 | 105 | 0 | 200 | 0 | 1 | 4 | 4 | 4 | 4 | 4 |
| 3 | | 1380 | 5 | 1500 | 0 | 0 | 1.5 | 4 | 4 | 4 | 4 | 4 |
| 4 | | 1630 | 105 | 2250 | 0 | 0 | 2 | 3 | 3.5 | 4 | 4 | 4 |

It will be appreciated that samples including higher concentrations of IPBC, MIT, or carbendazim not in combination with all three preservatives exhibited lower anti-microbial effectiveness and more microbial growth as compared to a sample that contained all three preservatives (sample 4). It also will be appreciated that the sample (4), which included high concentrations of IPBC, MIT, and Carbendazim, provided superior effectiveness over time as compared to existing formulations (Control).

Example III: Comparison of Novel Preservation Package to Existing Preservatives

Samples of commercially available water-borne magenta and universal blue colorant compositions containing the following conventional humectants, extenders/dispersants, surfactants, thickeners, pH buffers, and inert pigments were prepared.

TABLE 7

Composition of Commercially Available Magenta and Blue Colorant Compositions in Weight Percent

| | Water-borne Magenta | Universal Blue |
|---|---|---|
| Water | 53.1 | 36.0 |
| Humectant | 3.8 | 11.6 |
| Extender/Dispersent | 10.0 | 13.7 |
| Defoamer | 0.3 | 0.9 |
| Surfactant | 3.3 | 7.7 |
| Thickener | 1.4 | 2.3 |
| pH Buffer | 0.0 | 0.2 |
| Inert Pigment | 14.8 | 17.1 |
| Magenta Pigment | 12.3 | 0.0 |
| Blue Pigment | 0.0 | 9.0 |

Preservatives were added to the colorant compositions to yield active biocide agents present in the colorant compositions at the following concentrations, and the modified colorant compositions were ground using zirconium milling beads to a 7 Hegman fineness of grind value.

TABLE 8

Additional Preservatives in Colorant Compositions

| | Preservative Concentration (ppm by weight) | | | |
|---|---|---|---|---|
| | Water-only Magenta Control | Water-only Magenta Test | Universal Blue Control | Universal Blue Test |
| IPBC | 852 | 1513 | 727 | 1363 |
| MIT | 5 | 101 | 105 | 91 |

TABLE 8-continued

Additional Preservatives in Colorant Compositions

| | Preservative Concentration (ppm by weight) | | | |
|---|---|---|---|---|
| | Water-only Magenta Control | Water-only Magenta Test | Universal Blue Control | Universal Blue Test |
| CMIT | 18 | 37 | 36 | 33 |
| BIT | 0 | 561 | 586 | 506 |
| Zinc Pyrithione | 798 | 0 | 1520 | 0 |
| Carbendazim | 0 | 862 | 0 | 777 |

Figure 2:
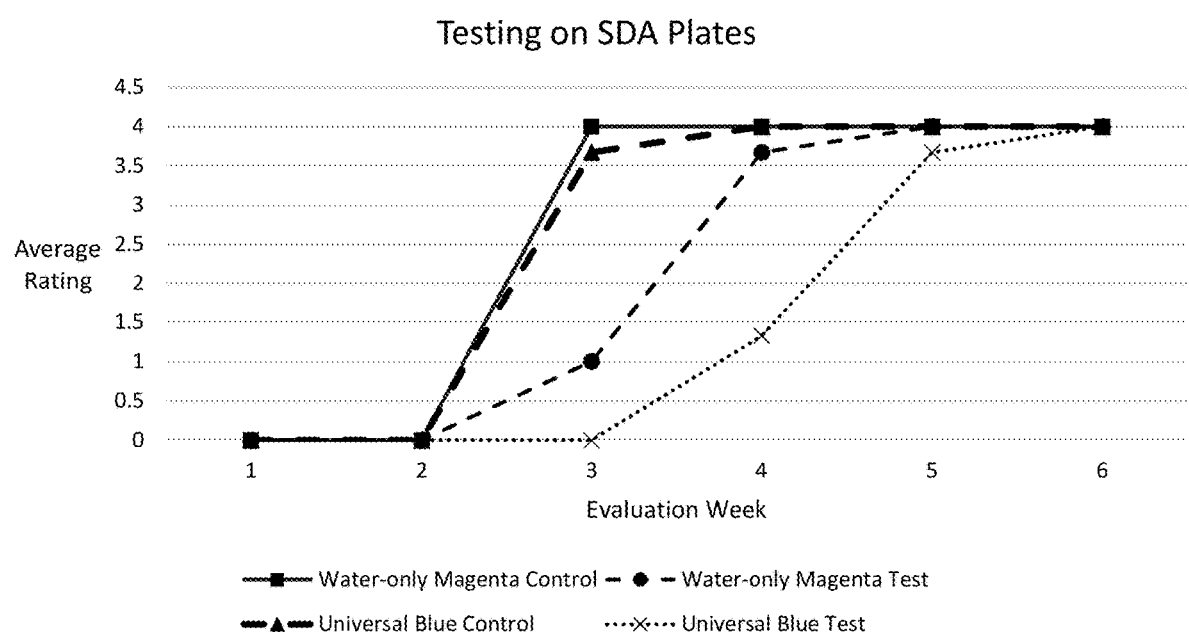
FIG. 2 is a plot of the antimicrobial efficacy of colorant compositions of the present disclosure as compared to commercially-available, water-borne colorant compositions as evaluated on SDA plates.

The antimicrobial efficacy was tested using the novel method described herein, with samples in triplicate. Parallel testing was performed to evaluate growth on TSA plates and SDA plates. The samples were evaluated weekly, with average results shown in FIG. 1and FIG. 2.

The test results show that the novel preservative package including high levels of MIT, IPBC, and carbendazim provided increased resistance to microbial growth as compared to a control colorant composition that comprises BIT and zinc pyrithione.

What is claimed is:

1. A colorant composition comprising:
an alkyl-isothiazolin-3-one in an amount from about 25 ppm to about 200 ppm based on the total weight of components of the composition, having a structure

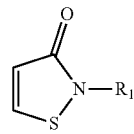

where $R_1$ is a linear or branched chain alkyl group having 1-8 carbons; and
a halo-propynyl alkylcarbamate having the structure

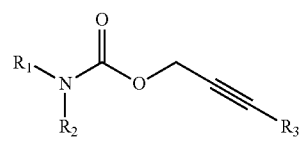

where $R_1$ and $R_2$ are H or linear or branched chain alkyl groups having 1-7 carbons, and where $R_3$ is a halogen atom (F, Cl, Br, I, or At) in an amount from about 1,000 ppm to about 10,000 ppm based on the total weight of components of the composition; and
a secondary amino-benzimidazole having the structure

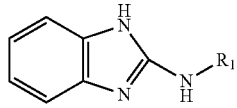

where $R_1$ is a carboxylate or ester group in an amount from about 500 ppm to about 4,000 ppm based on the total weight of components of the composition;
wherein the colorant composition contains less than 200 g/L VOCs; and
wherein the colorant composition comprises one or more pigments and a carrier and is substantially free of a film-forming polymer;
and wherein the colorant composition is a colorant for tinting a base coating composition.

2. The colorant composition of claim 1,
wherein the alkyl-isothiazolin-3-one is present in an amount of greater than 75 ppm based on the total weight of components of the composition.

3. The colorant composition of claim 2,
wherein the alkyl-isothiazolin-3-one is present in an amount greater than 125 ppm based on the total weight of components of the composition.

4. The colorant composition of claim 1,
wherein the alkyl-isothiazolin-3-one is present in an amount less than 150 ppm based on the total weight of components of the composition.

5. The colorant composition of claim 1,
wherein the halo-propynyl alkylcarbamate is present in an amount greater than 2500 ppm based on the total weight of components of the composition.

6. The colorant composition of claim 5,
wherein the halo-propynyl alkylcarbamate is present in an amount greater than 5000 ppm based on the total weight of components of the composition.

7. The colorant composition of claim 1,
wherein the halo-propynyl alkylcarbamate is present in an amount less than 7500 ppm based on the total weight of components of the composition.

8. The colorant composition of claim 1, wherein the secondary amino-benzimidazole is present in an amount greater than 1,500 ppm based on the total weight of components of the composition.

9. The colorant composition of claim 8, wherein the secondary amino-benzimidazole is present in an amount greater than 2,500 ppm based on the total weight of components of the composition.

10. The colorant composition of claim 1, wherein the secondary amino-benzimidazole is present in an amount less than 3,000 ppm based on the total weight of components of the composition.

11. The colorant composition of claim 1, wherein the alkyl-isothiazolin-3-one is 2-methyl-4-isothiazolin-3-one.

12. The colorant composition of claim 1, wherein the halo-propynyl alkylcarbamate is 3-iodo-2-propynyl butyl carbamate.

13. The colorant composition of claim 1,
wherein the secondary amino-benzimidazole is carbendazim.

14. The colorant composition of claim 1,
wherein the colorant composition contains less than 100 g/L VOCs.

15. The colorant composition of claim 1, wherein the colorant composition has a spore coverage rating of three or less according to a Colorant Microbial Resistance Test as described herein following three weeks of incubation.

16. The colorant composition of claim 1,
wherein the colorant composition is substantially free of an alkyl-isothiazolin-3-one that is not a methyl-isothiazolin-3-one.

17. The colorant composition of claim 1,
wherein the colorant composition is substantially free of a pyrithione.

18. The colorant composition of claim 1,
wherein the colorant composition is substantially free of zinc oxide.

19. The colorant composition of claim 1,
wherein the colorant composition comprises a polyether humectant.

20. The colorant composition of claim 1,
wherein the base coating composition is a latex paint.

* * * * *